United States Patent
Wales

(10) Patent No.: US 7,828,186 B2
(45) Date of Patent: Nov. 9, 2010

(54) SURGICAL INSTRUMENT INCORPORATING A FLUID TRANSFER CONTROLLED ARTICULATION BLADDER AND METHOD OF MANUFACTURE

(75) Inventor: Kenneth S. Wales, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 77 days.

(21) Appl. No.: 11/239,528

(22) Filed: Sep. 28, 2005

(65) Prior Publication Data

US 2006/0190032 A1   Aug. 24, 2006

Related U.S. Application Data

(63) Continuation-in-part of application No. 11/061,908, filed on Feb. 18, 2005.

(51) Int. Cl.
*A61B 17/072* (2006.01)
(52) U.S. Cl. .................. 227/175.1; 227/176.1; 227/19
(58) Field of Classification Search ... 227/175.1–182.1, 227/19; 606/219
See application file for complete search history.

(56) References Cited

U.S. PATENT DOCUMENTS

| | | | |
|---|---|---|---|
| 3,506,005 A * | 4/1970 | MacCarone et al. ......... | 604/132 |
| 3,726,134 A | 4/1973 | Grabovac | |
| 4,331,277 A | 5/1982 | Green et al. | |
| 4,485,817 A | 12/1984 | Swiggett | |
| 4,488,523 A | 12/1984 | Schichman | |
| 4,794,912 A * | 1/1989 | Lia ............................. | 600/152 |
| 4,921,482 A | 5/1990 | Hammerslag et al. | |
| 5,005,754 A * | 4/1991 | Van Overloop .......... | 227/178.1 |
| 5,018,657 A * | 5/1991 | Pedlick et al. ........... | 227/178.1 |
| 5,179,934 A | 1/1993 | Nagayoshi et al. | |
| 5,197,649 A | 3/1993 | Bessler et al. | |
| 5,219,111 A * | 6/1993 | Bilotti et al. ............. | 227/175.1 |
| 5,250,074 A | 10/1993 | Wilk et al. | |
| 5,275,608 A | 1/1994 | Forman et al. | |
| 5,312,023 A | 5/1994 | Green et al. | |
| 5,314,466 A | 5/1994 | Stern et al. | |
| 5,330,502 A | 7/1994 | Hassler et al. | |

(Continued)

FOREIGN PATENT DOCUMENTS

EP         071959        2/1983

(Continued)

OTHER PUBLICATIONS

EPO Search Report, Application No. 06 25 0869, Jun. 19, 2006, pp. 1-4.

(Continued)

*Primary Examiner*—Rinaldi I. Rada
*Assistant Examiner*—Lindsay Low

(57) ABSTRACT

A surgical instrument particularly suited to endoscopic use articulates an end effector by including a fluid transfer articulation mechanism that is proximally controlled. A fluid control, which is attached to a proximal portion, transfers fluid through the elongate shaft through a first fluid passage to a first fluid actuator that responds by articulating an articulation joint. Two opposing fluid actuators may respond to differential fluid transfer to effect articulation. Thereby, design flexibility is achieved by avoiding the design constraints of transferring a mechanical motion through the tight confines of the elongate shaft sufficient to effect articulation.

31 Claims, 8 Drawing Sheets

U.S. PATENT DOCUMENTS

| | | | |
|---|---|---|---|
| 5,339,723 A | 8/1994 | Huitema | |
| 5,356,064 A | 10/1994 | Green et al. | |
| 5,361,583 A | 11/1994 | Huitema | |
| 5,381,943 A | 1/1995 | Allen et al. | |
| 5,405,344 A | 4/1995 | Williamson et al. | |
| 5,409,498 A | 4/1995 | Braddock et al. | |
| 5,411,508 A | 5/1995 | Bessler et al. | |
| 5,411,519 A | 5/1995 | Tovey et al. | |
| 5,441,494 A | 8/1995 | Ortiz | |
| 5,456,401 A | 10/1995 | Green et al. | |
| 5,456,684 A | 10/1995 | Schmidt et al. | |
| 5,465,895 A | 11/1995 | Knodel et al. | |
| 5,468,250 A | 11/1995 | Paraschac et al. | |
| 5,482,197 A | 1/1996 | Green et al. | |
| 5,485,952 A | 1/1996 | Fontayne | |
| 5,518,164 A | 5/1996 | Hooven | |
| 5,520,678 A | 5/1996 | Heckele et al. | |
| 5,530,502 A | 6/1996 | Petruchik | |
| 5,547,117 A | 8/1996 | Hamblin et al. | |
| 5,562,682 A | 10/1996 | Oberlin et al. | |
| 5,573,543 A | 11/1996 | Akopov et al. | |
| 5,575,799 A | 11/1996 | Bolanos et al. | |
| 5,601,572 A | 2/1997 | Middleman et al. | |
| 5,620,649 A * | 4/1997 | Trotta | 264/515 |
| 5,632,433 A | 5/1997 | Grant et al. | |
| 5,662,662 A | 9/1997 | Bishop et al. | |
| 5,669,544 A | 9/1997 | Schulze et al. | |
| 5,673,840 A | 10/1997 | Schulze et al. | |
| 5,673,841 A | 10/1997 | Schulze et al. | |
| 5,690,269 A | 11/1997 | Bolanos et al. | |
| 5,692,668 A * | 12/1997 | Schulze et al. | 227/175.1 |
| 5,702,408 A | 12/1997 | Wales et al. | |
| 5,743,456 A | 4/1998 | Jones et al. | |
| 5,752,973 A | 5/1998 | Kieturakis | |
| 5,762,255 A | 6/1998 | Chrisman et al. | |
| 5,779,727 A | 7/1998 | Orejola et al. | |
| 5,782,859 A | 7/1998 | Nicholas et al. | |
| 5,797,536 A | 8/1998 | Smith et al. | |
| 5,797,537 A | 8/1998 | Oberlin et al. | |
| 5,826,776 A | 10/1998 | Schulze et al. | |
| 5,829,662 A | 11/1998 | Allen et al. | |
| 5,860,995 A | 1/1999 | Berkelaar | |
| 5,865,361 A | 2/1999 | Milliman et al. | |
| 5,901,895 A | 5/1999 | Heaton et al. | |
| 5,918,791 A | 7/1999 | Sorrentino et al. | |
| 6,010,054 A | 1/2000 | Johnson et al. | |
| 6,139,508 A | 10/2000 | Simpson et al. | |
| 6,460,749 B1 | 10/2002 | Levinson et al. | |
| 6,485,409 B1 | 11/2002 | Voloshin et al. | |
| 6,488,197 B1 | 12/2002 | Whitman | |
| 6,506,202 B1 * | 1/2003 | Dutta et al. | 606/194 |
| 6,666,854 B1 | 12/2003 | Lange | |
| 6,667,825 B2 | 12/2003 | Lu et al. | |
| 6,669,073 B2 | 12/2003 | Milliman et al. | |
| 6,715,259 B2 | 4/2004 | Johnston et al. | |
| 6,755,338 B2 | 6/2004 | Hahnen et al. | |
| 6,756,094 B1 * | 6/2004 | Wang et al. | 428/36.9 |
| 6,786,382 B1 | 9/2004 | Hoffman | |
| 6,830,174 B2 | 12/2004 | Hillstead et al. | |
| 6,877,647 B2 | 4/2005 | Green et al. | |
| 6,905,057 B2 | 6/2005 | Swayze et al. | |
| 6,951,675 B2 * | 10/2005 | Chin et al. | 428/35.7 |
| 6,953,139 B2 | 10/2005 | Milliman et al. | |
| 6,964,363 B2 | 11/2005 | Wales et al. | |
| 6,978,921 B2 | 12/2005 | Shelton | |
| 6,981,628 B2 | 1/2006 | Wales | |
| 7,087,052 B2 | 8/2006 | Sampson et al. | |
| 7,087,071 B2 | 8/2006 | Nicholas et al. | |
| 7,111,769 B2 | 9/2006 | Wales et al. | |
| 7,112,357 B2 * | 9/2006 | Miller et al. | 428/36.92 |
| 7,159,750 B2 | 1/2007 | Racenet et al. | |
| 7,166,077 B2 * | 1/2007 | Millay et al. | 600/499 |
| 7,213,736 B2 | 5/2007 | Wales et al. | |
| 7,407,074 B2 | 8/2008 | Ortiz et al. | |
| 7,410,086 B2 | 8/2008 | Ortiz et al. | |
| 7,481,824 B2 | 1/2009 | Gillum et al. | |
| 7,588,177 B2 | 9/2009 | Racenet | |
| 2003/0111507 A1 * | 6/2003 | Nunez | 227/180.1 |
| 2003/0045900 A1 | 9/2003 | Hahnen | |
| 2003/0178848 A1 | 9/2003 | Williams | |
| 2004/0002726 A1 | 1/2004 | Nunez et al. | |
| 2004/0108357 A1 | 6/2004 | Milliman et al. | |
| 2004/0173659 A1 | 9/2004 | Green et al. | |
| 2004/0179244 A1 | 9/2004 | Lai | |
| 2004/0232196 A1 | 11/2004 | Shelton et al. | |
| 2004/0232197 A1 | 11/2004 | Shelton et al. | |
| 2004/0232201 A1 | 11/2004 | Wenchell et al. | |
| 2004/0243176 A1 | 12/2004 | Hahnen et al. | |
| 2005/0006429 A1 | 1/2005 | Wales et al. | |
| 2005/0006430 A1 | 1/2005 | Wales | |
| 2005/0006432 A1 | 1/2005 | Racenet et al. | |
| 2005/0006434 A1 | 1/2005 | Wales et al. | |
| 2005/0070958 A1 | 3/2005 | Swayze et al. | |
| 2005/0107824 A1 | 5/2005 | Hillstead et al. | |
| 2005/0165415 A1 | 7/2005 | Wales | |
| 2005/0263562 A1 | 12/2005 | Shelton | |
| 2006/0011699 A1 | 1/2006 | Olson et al. | |
| 2006/0016853 A1 | 1/2006 | Racenet | |
| 2006/0022014 A1 | 2/2006 | Shelton, IV et al. | |
| 2006/0022015 A1 | 2/2006 | Shelton, IV et al. | |
| 2006/0025809 A1 | 2/2006 | Shelton, IV | |
| 2006/0025810 A1 | 2/2006 | Shelton, IV | |
| 2006/0025811 A1 | 2/2006 | Shelton, IV | |
| 2006/0025813 A1 | 2/2006 | Shelton et al. | |
| 2006/0025817 A1 | 2/2006 | Ortiz et al. | |
| 2006/0041273 A1 | 2/2006 | Ortiz et al. | |
| 2006/0047307 A1 | 3/2006 | Ortiz et al. | |
| 2006/0047308 A1 * | 3/2006 | Ortiz et al. | 606/219 |
| 2006/0089535 A1 | 4/2006 | Raz et al. | |
| 2006/0190028 A1 | 8/2006 | Wales | |
| 2006/0190032 A1 | 8/2006 | Wales | |
| 2006/0226196 A1 * | 10/2006 | Hueil et al. | 227/175.1 |
| 2006/0229665 A1 | 10/2006 | Wales et al. | |
| 2006/0259071 A1 | 11/2006 | Nicholas et al. | |
| 2006/0289600 A1 * | 12/2006 | Wales et al. | 227/175.1 |
| 2006/0289602 A1 | 12/2006 | Wales et al. | |
| 2007/0027468 A1 | 2/2007 | Wales et al. | |
| 2007/0152014 A1 * | 7/2007 | Gillum et al. | 227/175.1 |

FOREIGN PATENT DOCUMENTS

| | | |
|---|---|---|
| EP | 0 324 635 | 7/1989 |
| EP | 0 598 976 | 6/1994 |
| EP | 0717959 | 6/1996 |
| EP | 0769273 | 4/1997 |
| EP | 0807409 | 11/1997 |
| EP | 0 603 472 | 6/2004 |
| EP | 1495726 | 1/2005 |
| EP | 1 522 263 | 4/2005 |
| EP | 1627605 | 2/2006 |
| EP | 1 693 008 | 8/2006 |
| EP | 1693008 | 8/2006 |
| EP | 1 785 098 | 5/2007 |
| WO | WO 01/93766 | 12/2001 |
| WO | WO 02/062241 | 8/2002 |
| WO | WO 03/013374 | 2/2003 |
| WO | WO 03/101313 | 12/2003 |
| WO | WO 2004/002327 | 1/2004 |
| WO | WO 2004/006980 | 1/2004 |
| WO | WO 2004/032762 | 4/2004 |

| | | |
|---|---|---|
| WO | WO 2004/112618 | 12/2004 |

OTHER PUBLICATIONS

EPO Search Report, Application No. 06253759.2, Nov. 24, 2006, pp. 1-5.
EPO Search Report, Application No. 06250869.2, Jul. 13, 2006, pp. 1-4.
Australian Search Report for Application No. SG 200600909-6, dated Mar. 2, 2007.
Australian Search Report for Application No. SG 200601987-1, dated Feb. 8, 2007.
Danish Search Report for Application No. 200601986-3, dated Apr. 11, 2007.
European Search Report dated Aug. 8, 2007 for EPO Application No. 06251959.
European Search Report dated Jul. 19, 2007 for EPO Application No. 06253226.
European Search Report dated Aug. 21, 2007 for EPO Application No. 06254005.
European Search Report dated Nov. 23, 2007 for EPO Application No. 06253224.
Notice of Allowance dated Nov. 15, 2006 for U.S. Appl. No. 11/100,847.
Notice of Allowance dated Oct. 5, 2007 for U.S. Appl. No. 11/061,908.
Notice of Allowance dated Nov. 30, 2007 for U.S. Appl. No. 11/100,847.
Office Action dated Jun. 1, 2006 for U.S. Appl. No. 11/100,847.
Office Action dated Sep. 27, 2006 for U.S. Appl. No. 11/164,094.
Office Action dated Dec. 6, 2006 for U.S. Appl. No. 11/061,908.
Office Action dated Mar. 9, 2007 for U.S. Appl. No. 11/061,908.
Office Action dated Mar. 29, 2007 for U.S. Appl. No. 11/165,094.
Office Action dated Jun. 4, 2007 for U.S. Appl. No. 11/165,094.
Office Action dated Jun. 26, 2007 for U.S. Appl. No. 11/239,528.
Office Action dated Aug. 1, 2007 for U.S. Appl. No. 11/100,847.
Office Action dated Aug. 23, 2007 for U.S. Appl. No. 11/165,094.
Office Action dated Sep. 7, 2007 for U.S. Appl. No. 11/238,358.
European Search Report dated Nov. 20, 2006 for Applciation No. 06254005.9.
Notice of Allowance dated Nov. 6, 2007 for U.S. Appl. No. 11/061,908.
Notice of Allowance dated Feb. 20, 2008 for U.S. Appl. No. 11/061,908.
Notice of Allowance dated Jun. 26, 2008 for U.S. Appl. No. 11/165,094.
Notice of Allowance dated Jul. 31, 2008 for U.S. Appl. No. 11/238,358.
Final Rejection dated Feb. 25, 2008 for U.S. Appl. No. 11/165,094.
Final Rejection dated Mar. 26, 2008 for U.S. Appl. No. 11/238,358.
Non-Final Rejection dated Apr. 7, 2008 for U.S. Appl. No. 11/165,468.
Non-Final Rejection dated Jul. 17, 2008 for U.S. Appl. No. 11/100,772.
EPO Search Report dated Jul. 28, 2006 for Application No. 06253224.
EPO Search Report dated Aug. 31, 2006 for Application No. 06253226.
EPO Search Report dated Nov. 6, 2006 for Application No. 06253759.
EPO Search Report dated Nov. 20, 2006 for Application No. 06254005.
EPO Search Report dated May 5, 2008 for Application No. 06251960.

* cited by examiner

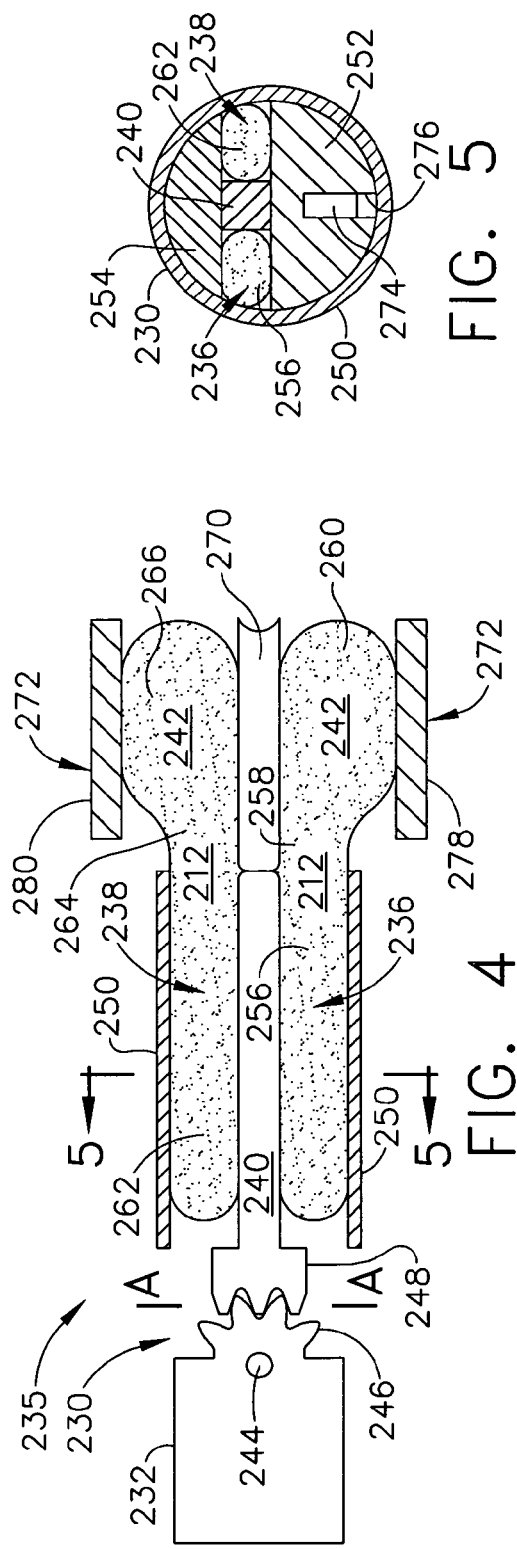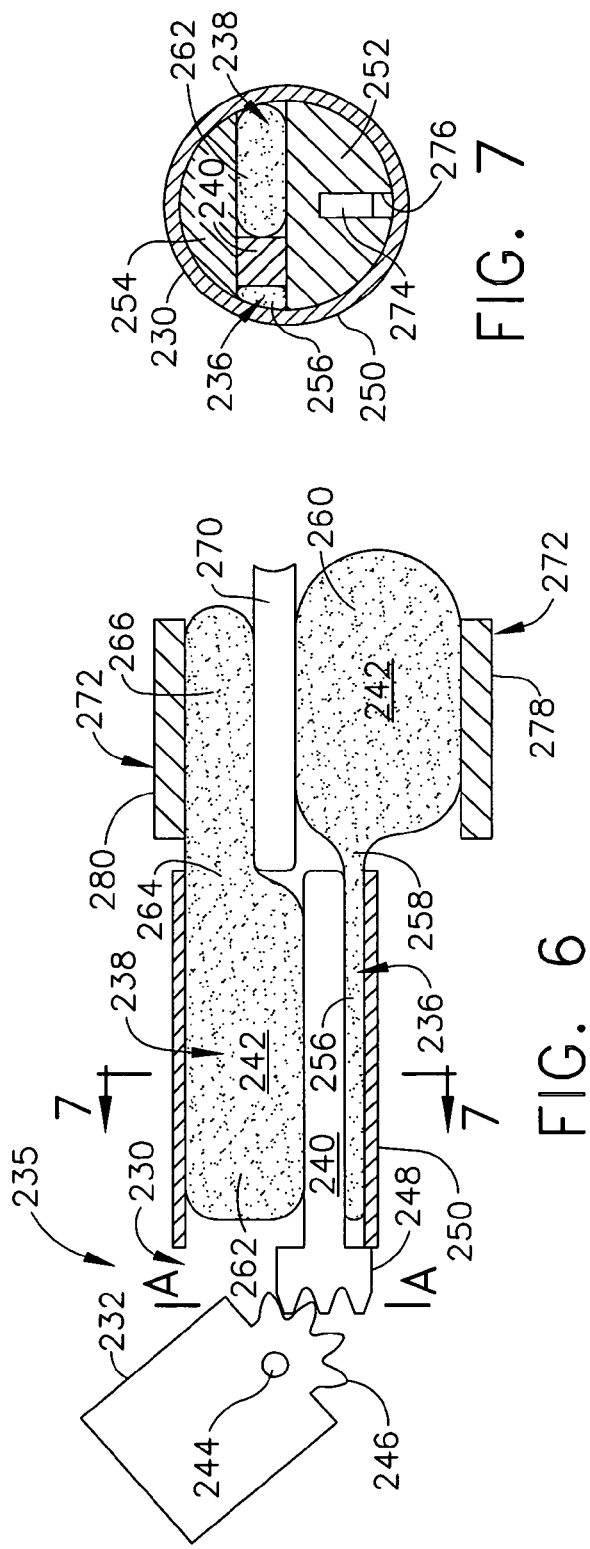

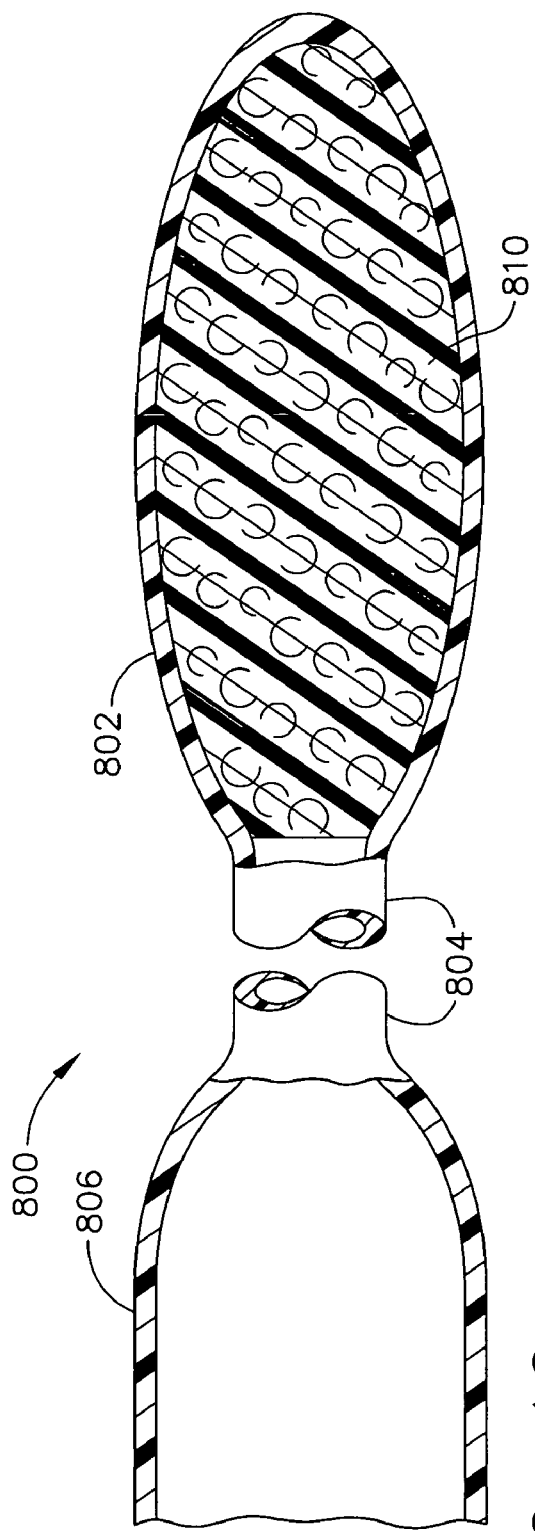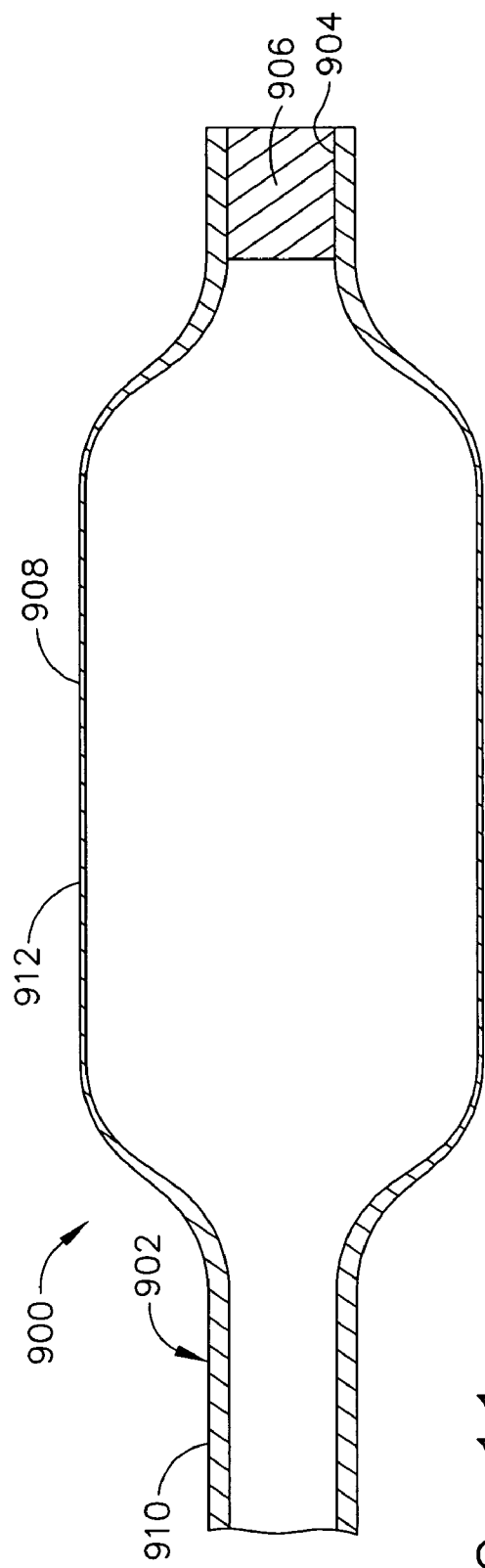

SURGICAL INSTRUMENT INCORPORATING A FLUID TRANSFER CONTROLLED ARTICULATION BLADDER AND METHOD OF MANUFACTURE

CROSS REFERENCE TO RELATED APPLICATIONS

The present invention is a continuation-in-part application of commonly owned U.S. patent application Ser. No. 11/061,908 entitled "SURGICAL INSTRUMENT INCORPORATING A FLUID TRANSFER CONTROLLED ARTICULATION MECHANISM" to Kenneth Wales and Chad Boudreaux filed on 18 Feb. 2005, the disclosure of which is hereby incorporated by reference in its entirety.

FIELD OF THE INVENTION

The present invention relates in general to surgical instruments that are suitable for endoscopically inserting an end effector (e.g., endocutter, grasper, cutter, staplers, clip applier, access device, drug/gene therapy delivery device, and an energy device using ultrasound, RF, laser, etc.) to a surgical site, and more particularly to such surgical instruments with an articulating shaft.

BACKGROUND OF THE INVENTION

Endoscopic surgical instruments are often preferred over traditional open surgical devices since a smaller incision tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

The positioning of the end effector is constrained by the trocar. Generally, these endoscopic surgical instruments include a long shaft between the end effector and a handle portion manipulated by the clinician. This long shaft enables insertion to a desired depth and rotation about the longitudinal axis of the shaft, thereby positioning the end effector to a degree. With judicious placement of the trocar and use of graspers, for instance, through another trocar, often this amount of positioning is sufficient. Surgical stapling and severing instruments, such as described in U.S. Pat. No. 5,465,895, are an example of an endoscopic surgical instrument that successfully positions an end effector by insertion and rotation.

More recently, U.S. patent application Ser. No. 10/443,617, "SURGICAL STAPLING INSTRUMENT INCORPORATING AN E-BEAM FIRING MECHANISM" to Shelton IV et al., filed on 20 May 2003, which is hereby incorporated by reference in its entirety, describes an improved "E-beam" firing bar for severing tissue and actuating staples. Some of the additional advantages include affirmatively spacing the jaws of the end effector, or more specifically a staple applying assembly, even if slightly too much or too little tissue is clamped for optimal staple formation. Moreover, the E-beam firing bar engages the end effector and staple cartridge in a way that enables several beneficial lockouts to be incorporated.

Depending upon the nature of the operation, it may be desirable to further adjust the positioning of the end effector of an endoscopic surgical instrument. In particular, it is often desirable to orient the end effector at an axis transverse to the longitudinal axis of the shaft of the instrument. The transverse movement of the end effector relative to the instrument shaft is conventionally referred to as "articulation". This is typically accomplished by a pivot (or articulation) joint being placed in the extended shaft just proximal to the staple applying assembly. This allows the surgeon to articulate the staple applying assembly remotely to either side for better surgical placement of the staple lines and easier tissue manipulation and orientation. This articulated positioning permits the clinician to more easily engage tissue in some instances, such as behind an organ. In addition, articulated positioning advantageously allows an endoscope to be positioned behind the end effector without being blocked by the instrument shaft.

Approaches to articulating a surgical stapling and severing instrument tend to be complicated by integrating control of the articulation along with the control of closing the end effector to clamp tissue and fire the end effector (i.e., stapling and severing) within the small diameter constraints of an endoscopic instrument. Generally, the three control motions are all transferred through the shaft as longitudinal translations. For instance, U.S. Pat. No. 5,673,840 discloses an accordion-like articulation mechanism ("flex-neck") that is articulated by selectively drawing back one of two connecting rods through the implement shaft, each rod offset respectively on opposite sides of the shaft centerline. The connecting rods ratchet through a series of discrete positions.

Another example of longitudinal control of an articulation mechanism is U.S. Pat. No. 5,865,361 that includes an articulation link offset from a camming pivot such that pushing or pulling longitudinal translation of the articulation link effects articulation to a respective side. Similarly, U.S. Pat. No. 5,797,537 discloses a similar rod passing through the shaft to effect articulation.

In co-pending and commonly owned U.S. patent application Ser. No. 10/615,973 "SURGICAL INSTRUMENT INCORPORATING AN ARTICULATION MECHANISM HAVING ROTATION ABOUT THE LONGITUDINAL AXIS" to Frederick E. Shelton IV et al, the disclosure of which is hereby incorporated by reference in its entirety, a rotational motion is used to transfer articulation motion as an alternative to a longitudinal motion.

While these mechanically communicated articulation motions have successfully enabled an endoscopic surgical stapling and severing instrument to articulate, development trends pose numerous challenges and barriers to entry into the market. Conflicting design objects include a shaft of as small a diameter as possible to reduce the size of the surgical opening yet with sufficient strength to perform the several motions (e.g., closing, firing, articulation, rotation, etc.). In addition, transferring sufficient force without binding and other frictional problems imposes design constraints that limit desirable features and reliability.

In U.S. Pat. No. 6,755,338, a medical instrument has a shaft that is manually deformable to a desired curved shape. To accommodate longitudinal clamping and firing motions down the deformable shaft, a pair of hydraulic lines pass down the shaft that are each part of a respective closed hydraulic system. Each hydraulic line communicates between a proximal piston moved by a trigger and a distal activator. The distal activator for clamping is a linearly moving piston that is proximally biased by a spring and mechanically connected to an end effector. The distal activator for firing is an actuation balloon that expands linearly in the distal direction. While linearly moving activators provide one way to cause actuation at a distal end of an implement portion of a medical portion, it may be desirable to produce another type of actuating motion.

Consequently, a significant need exists for a surgical instrument that incorporates an actuating mechanism that that may be incorporated within the close confines of an implement portion.

BRIEF SUMMARY OF THE INVENTION

The invention overcomes the above-noted and other deficiencies of the prior art by providing a surgical instrument having an implement portion that incorporates fluid bladders in the implement portion that reliably expand and contract in response to fluid transfer from a handle.

In one aspect of the invention, a surgical instrument has a handle having a control positionable to vary an internal volume of a reservoir with fluid transfer in relation to this volume change occurring through an elongate implement portion having a longitudinal axis sized for insertion through a cannula to reach internal tissue. An actuator changes in volume in relation to the fluid transfer and is positioned within a cavity in the implement portion to laterally actuate an actuating member. The actuator and/or the reservoir are advantageously formed of a bladder shaped for lateral actuation Thereby, fluid transfer control may be flexibly integrated into an elongate implement portion, avoiding various constraints on mechanical linkages that would otherwise be generally used.

In another aspect of the invention, a surgical instrument includes a compression surface movably attached to a handle to vary an internal volume of a reservoir bladder that performs fluid transfer in relation thereto to cause the actuation of the actuating bladder in the implement portion. Thereby, a closed fluid control system may be incorporated into a surgical instrument with desirable performance characteristics.

In yet another aspect of the invention, a surgical instrument includes a differential control in a handle to differentially vary fluid transfer from the fluid source to first and second conduits that respectively control first and second actuating bladders that work differentially in opposition against a motive surface of an actuated member attached to an elongate implement portion. Thereby, the advantages of selectively forcing the motive surface with similar force in either of two directions achieves responsive actuation of the implement portion as desired.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above and the detailed description of the embodiments given below, serve to explain the principles of the present invention.

FIG. 4 is a diagram of a laterally moving fluidic articulation mechanism with the rack and gear segment pivoting depicted in a nonarticulated state for the surgical instrument of FIG. 1.

FIG. 5 is cross-section, back view in elevation of the fluidic articulation mechanism of FIG. 11 taken along lines 5-5.

FIG. 6 is a diagram of the laterally moving fluidic articulation mechanism of FIG. 4 with the rack and gear segment pivoting depicted in an articulated state.

FIG. 7 is cross-section, back view in elevation of the fluidic articulation mechanism of FIG. 6 taken along lines 7-7.

FIG. 10 is a longitudinal cross section view of a communicating combination of a reservoir bladder and an actuating bladder for the surgical instrument of FIG. 1 with one bladder expansively biased by having open cell foam.

FIG. 11 is a longitudinal cross section view of a bladder for the surgical instrument of FIG. 1 formed from a plugged, heated and blown metal tube.

DETAILED DESCRIPTION OF THE INVENTION

Figure 1:
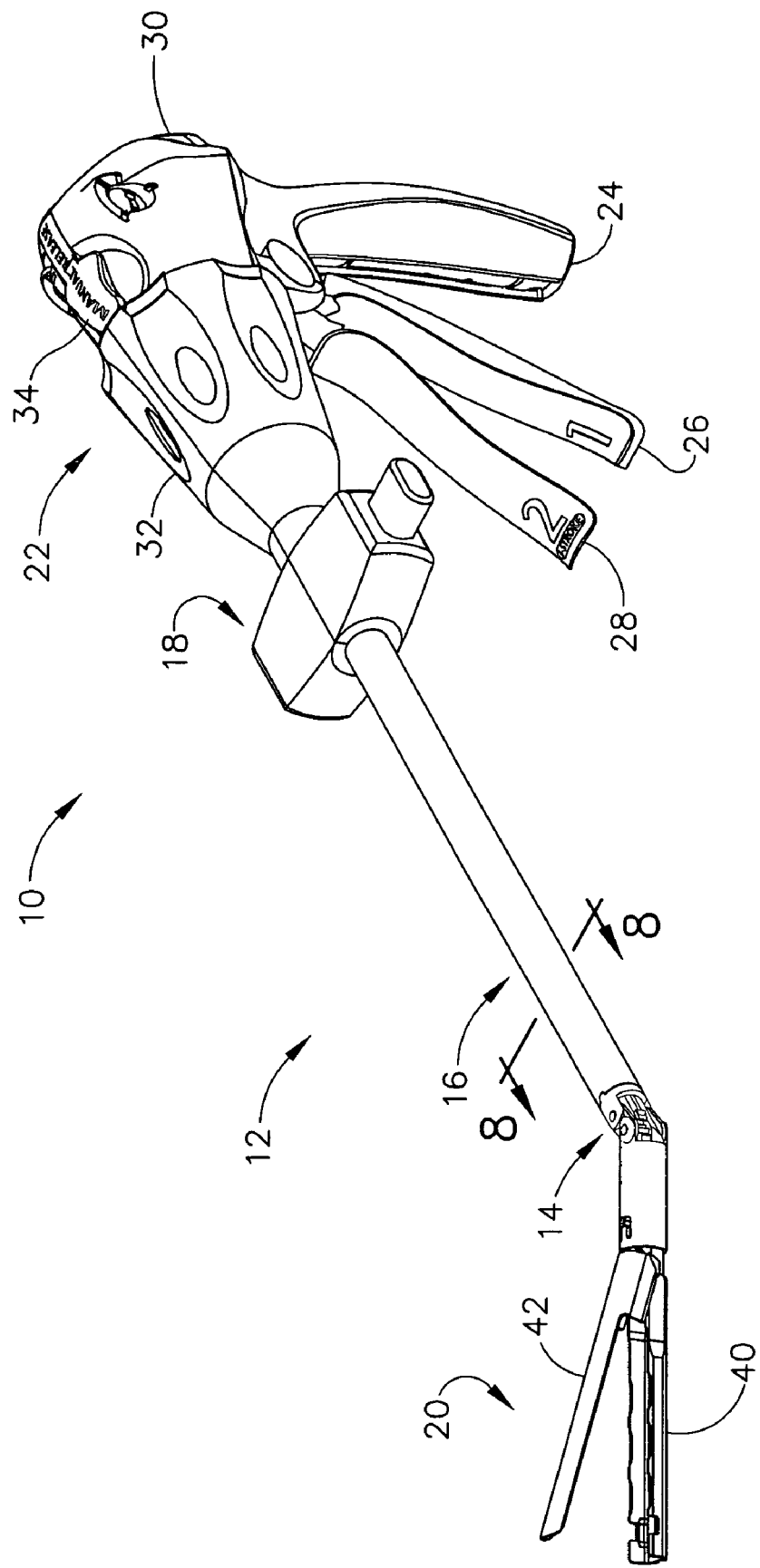
FIG. 1 is a front top perspective view of a surgical stapling and severing instrument shown with an open end effector, or staple applying assembly, with an articulation mechanism actuated by a fluidic actuation control, and with the staple cartridge removed.

Overview of articulating shaft. Turning to the Drawings, wherein like numerals denote like components throughout the several views, FIG. 1 depicts a surgical instrument, which in the illustrative versions is more particularly a surgical stapling and severing instrument 10, that is capable of practicing the unique benefits of the present invention. In particular, the surgical stapling and severing instrument 10 is sized for insertion, in a nonarticulated state as depicted in FIG. 1, through a trocar cannula passageway to a surgical site in a patient (not shown) for performing a surgical procedure. Once an implement portion 12 is inserted through a cannula passageway, an articulation mechanism 14 incorporated into a distal portion of an elongate shaft 16 of the implement portion 12 may be remotely articulated, as depicted in FIG. 1, by an articulation control 18. An end effector, depicted in the illustrative version as a staple applying assembly 20, is distally attached to the articulation mechanism 14. Thus, remotely articulating the articulation mechanism 14 thereby articulates the staple applying assembly 20 from a longitudinal axis of the elongate shaft 16. Such an angled position may have advantages in approaching tissue from a desired angle for severing and stapling, approaching tissue otherwise obstructed by other organs and tissue, and/or allowing an endoscope to be positioned behind and aligned with the staple applying assembly 20 for confirming placement.

Handle. The surgical and stapling and severing instrument 10 includes a handle portion 22 proximally connected to the implement portion 12 for providing positioning, articulation, closure and firing motions thereto. The handle portion 22 includes a pistol grip 24 toward which a closure trigger 26 is pivotally and proximally drawn by the clinician to cause clamping, or closing, of the staple applying assembly 20. A firing trigger 28 is farther outboard of the closure trigger 26 and is pivotally drawn by the clinician to cause the stapling and severing of clamped tissue clamped in the staple applying assembly 20. Thereafter, a closure release button 30 is depressed to release the clamped closure trigger 26, and thus the severed and stapled ends of the clamped tissue. The handle portion 22 also includes a rotation knob 32 coupled for movement with the elongate shaft 16 to rotate the shaft 16 and the articulated staple applying assembly 20 about the longitudinal axis of the shaft 16. The handle portion 22 also includes a firing refraction handle 34 to assist in retracting a firing mechanism (not depicted in FIG. 1) should binding occur, so that opening of the staple applying assembly 20 may occur thereafter.

It will be appreciated that the terms "proximal" and "distal" are used herein with reference to a clinician gripping a handle of an instrument. Thus, the surgical stapling assembly 20 is distal with respect to the more proximal handle portion 22. It will be further appreciated that, for convenience and clarity, spatial terms such as "vertical" and "horizontal" are used herein with respect to the drawings. However, surgical instruments are used in many orientations and positions, and these terms are not intended to be limiting and absolute.

An illustrative multi-stroke handle portion 22 for the surgical stapling and severing instrument 10 of FIG. 1 is described in greater detail in the co-pending and commonly-owned U.S. patent application entitled "SURGICAL STAPLING INSTRUMENT INCORPORATING A MULTI-STROKE FIRING POSITION INDICATOR AND RETRACTION MECHANISM" to Swayze and Shelton IV, Ser. No. 10/374,026, the disclosure of which is hereby incorporated by reference in its entirety, with additional features and variation as described herein. While a multi-stroke handle portion 22 advantageously supports applications with high firing forces over a long distance, applications consistent with the present invention may incorporate a single firing stroke, such as described in co-pending and commonly owned U.S. patent application "SURGICAL STAPLING INSTRUMENT HAVING SEPARATE DISTINCT CLOSING AND FIRING SYSTEMS" to Frederick E. Shelton IV, Michael E. Setser, and Brian J. Hemmelgarn, Ser. No. 10/441,632, the disclosure of which is hereby incorporated by reference in its entirety.

Figure 2:
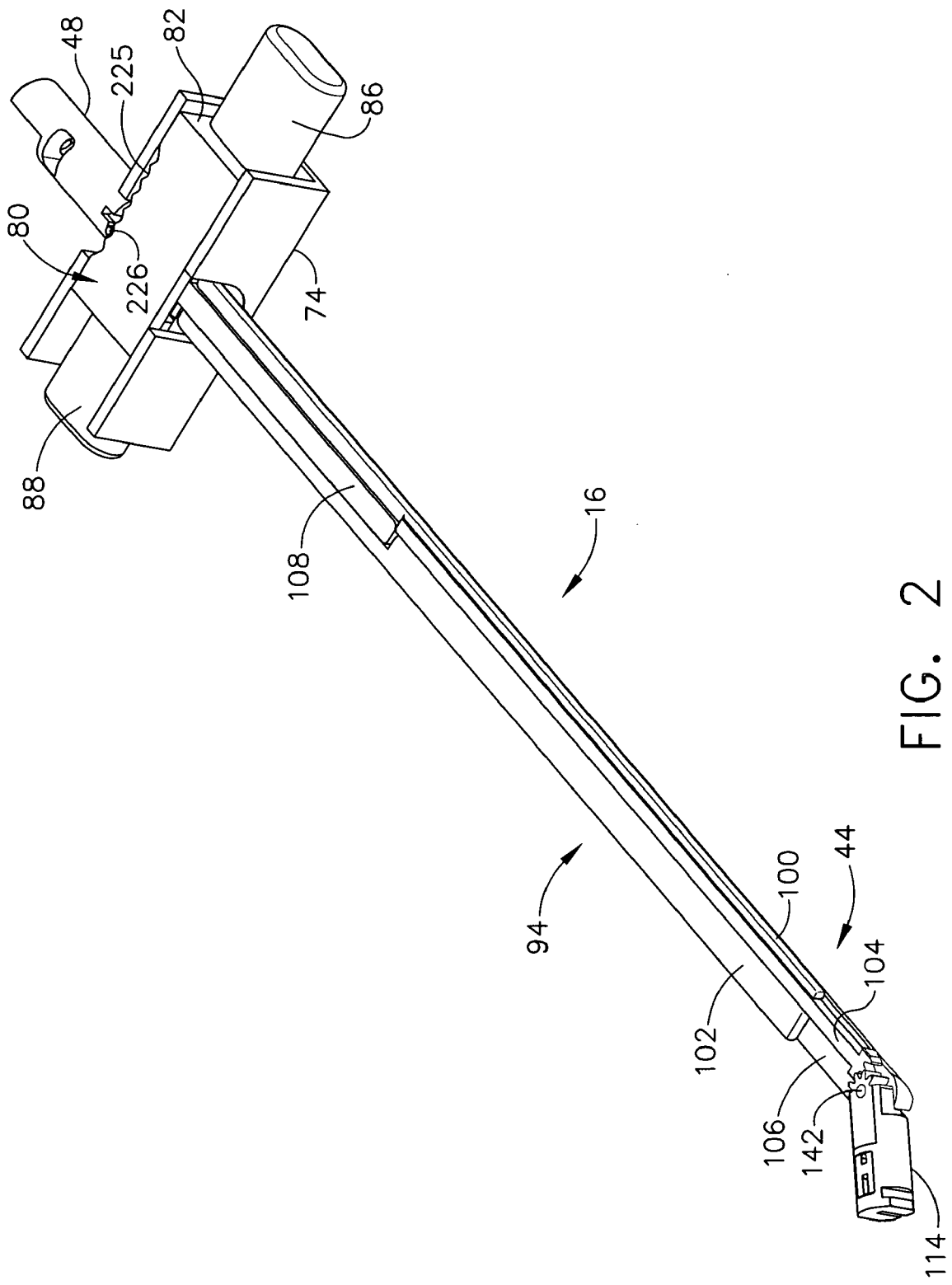
FIG. 2 is a front perspective view of an implement portion of the surgical instrument of FIG. 1 with a double pivot closure sleeve assembly and end effector removed to expose a single pivot frame ground articulated by a fluidic articulation mechanism.
Figure 3:
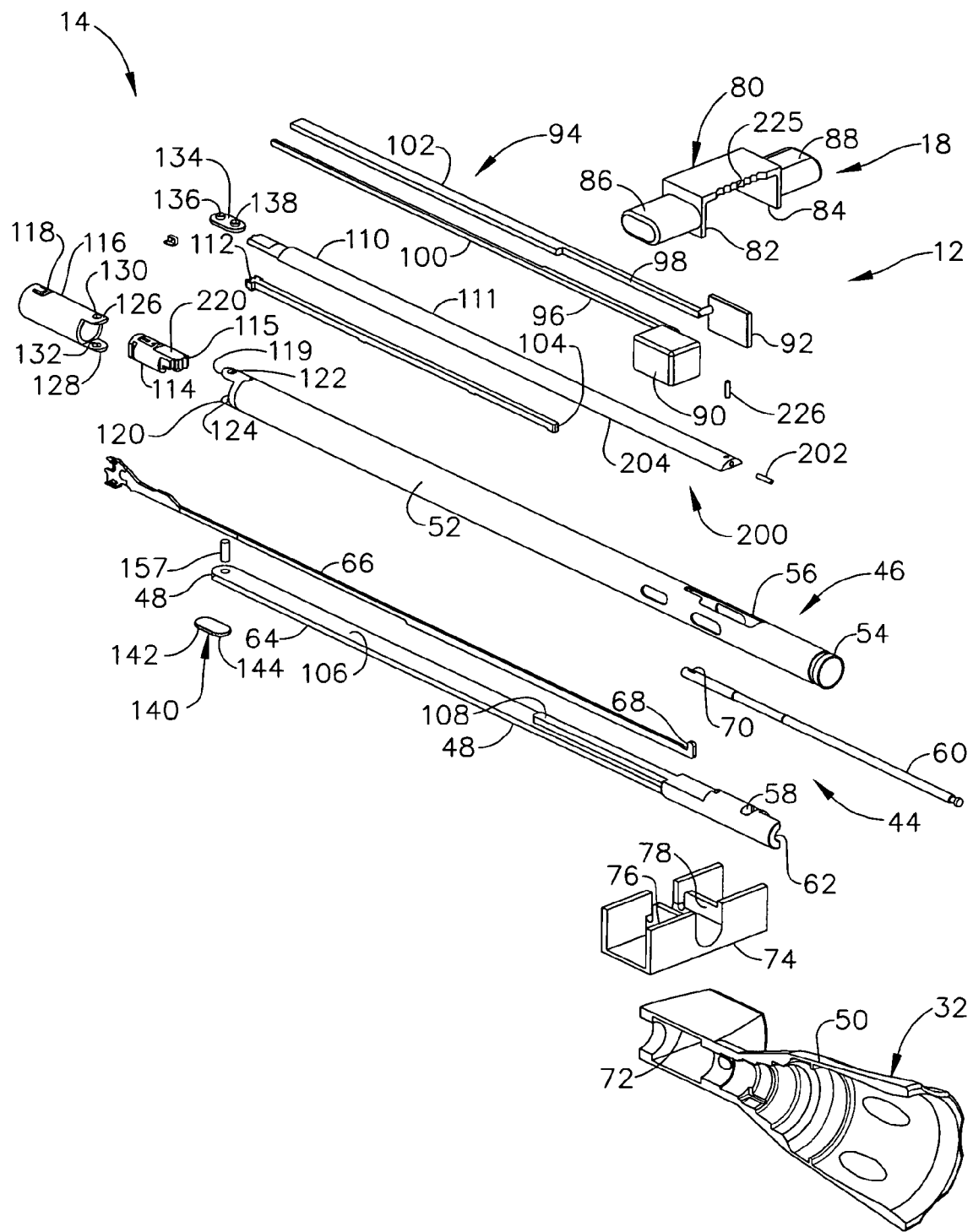
FIG. 3 is a perspective disassembled view of an elongate shaft and articulation mechanism of the surgical stapling and severing instrument of FIG. 1.

Implement portion (articulating elongate shaft and staple applying assembly). In FIGS. 1-3, the implement portion 12 advantageously incorporates the multiple actuation motions of longitudinal rotation, articulation, closure and firing within a small diameter suitable for endoscopic and laparoscopic procedures. The staple applying assembly 20 ("end effector") has a pair of pivotally opposed jaws, depicted as an elongate channel 40 with a pivotally attached anvil 42 (FIG. 1). Closure and clamping of the anvil 42 to the elongate channel 40 is achieved by longitudinally supporting the elongate channel 40 with a frame assembly 44 (FIG. 3) rotatably attached to the handle portion 22 over which a double pivot closure sleeve assembly 46 longitudinally moves to impart a closing and opening respectively to a distal and proximal motion to the anvil 42, even with the staple applying assembly 20 articulated as in FIG. 2.

The staple applying assembly 20 is described in greater detail in co-pending and commonly-owned U.S. patent application Ser. No. 10/955,042, "ARTICULATING SURGICAL STAPLING INSTRUMENT INCORPORATING A TWO-PIECE E-BEAM FIRING MECHANISM" to Frederick E. Shelton IV, et al., filed 30 Sep. 2004, the disclosure of which is hereby incorporated by reference in its entirety.

With particular reference to FIG. 3, the frame assembly 44 includes a single pivot frame ground 48 whose proximal end is engaged to the rotation knob 32, with a right half shell 50 thereon shown in FIG. 3. It should be appreciated that a proximal end of the closure sleeve assembly 46, specifically of a closure straight tube 52, encompasses the proximal end of the frame ground 48, passing further internally to the handle portion 22 to engage closure components (not shown) that longitudinally translate the closure sleeve assembly 46. A circular lip 54 at the proximal end of the closure straight tube 52 provides a rotating engagement to such components. Engaging components of the rotation knob 32 pass through a longitudinal slot 56 on a proximal portion of the straight closure tube 52 to engage an aperture 58 proximally positioned on the frame ground 48. The longitudinal slot 56 is of sufficient length to allow the closure longitudinal translation of the closure sleeve assembly 46 at various rotational angles set by the rotation knob 32 to the closure sleeve assembly 46 and the frame ground 48.

The elongate shaft 16 supports the firing motion by receiving a firing rod 60 that rotatingly engages firing components of the handle portion 22 (not shown). The firing rod 60 enters a proximal opening 62 along the longitudinal centerline of the frame ground 48. The distal portion of the frame ground 48 includes a firing bar slot 64 along its bottom that communicates with the proximal opening 62. A firing bar 66 longitudinally translates in the firing bar slot 64 and includes an upwardly projecting proximal pin 68 that engages a distal end 70 of the firing rod 60 to form a firing member.

The handle portion 22 supports articulation by incorporating a rectangular reservoir cavity 72, one lateral portion depicted in a distal portion of the rotation knob 32. A bottom compartment 74 that resides within the rectangular reservoir cavity 72 has laterally spaced apart left and right baffles 76, 78. An articulation actuator 80 slides laterally overtop of the bottom compartment 74, its downward laterally spaced left and right flanges 82, 84, which are outboard of the baffles 76, 78, each communicating laterally to left and right push buttons 86, 88 that extend outwardly from the respective shell halves of the rotation knob 32. The lateral movement of the articulation actuator 80 draws left and right flanges 82, 84 nearer and farther respectively to the left and right baffles 76, 78, operating against left and right reservoir bladders 90, 92 of a fluidic articulation system 94, each bladder 90, 92 communicating respectively and distally to left and right fluid conduits or passageways 96, 98 that in turn communicate respectively with left and right actuating bladders 100, 102. The latter oppose and laterally pivot a T-bar 104 of the articulation mechanism 14.

The frame assembly 44 constrains these fluidic actuations by including a top and distal recessed table 106 of the frame ground 48 upon which resides the fluid passages 96, 98 and actuating bladders 100, 102. The T-bar 104 also slidingly resides upon the recessed table 106 between the actuating bladders 100, 102. Proximal to the T-Bar 104, a raised barrier rib 108 is aligned thereto, serving to prevent inward expansion of the fluid passages 96, 98. The frame assembly 44 has a rounded top frame cover (spacer) 110 that slides overtop of the frame ground 48, preventing vertical expansion of the fluid passages 96, 98 and actuating bladders 100, 102, as well as constraining any vertical movement of the T-bar 104. In particular, the frame cover 110 includes features that enable it to also provide an articulation locking member 111.

A distal end ("rack") 112 of the T-bar 104 engages to pivot a proximally directed gear segment 115 of an articulated distal frame member 114 of the articulation mechanism 14. An articulating closure ring 116 encompasses the distal frame member 114 and includes a horseshoe aperture 118 that engages the anvil 42. A double pivoting attachment is formed between the closure straight tube 52 and articulating closure ring 116 over the articulating mechanism 14, allowing longitudinal closure motion even when the articulation mechanism 14 is articulated. In particular, top and bottom distally projecting pivot tabs 119, 120 on the closure straight tube 52 having pin holes 122, 124 respectively are longitudinally spaced away from corresponding top and bottom proximally projecting pivot tabs 126, 128 on the articulating closure ring 116 having pin holes 130, 132 respectively. An upper double pivot link 134 has longitudinally spaced upwardly directed distal and aft pins 136, 138 that engage pin holes 130, 122 respectively and a lower double pivot link 140 has longitudinally spaced downwardly projecting distal and aft pins 142, 144 that engage pin holes 132, 124 respectively In FIGS. 2-3, an articulation lock mechanism 200 is advantageously incorporated to maintain the staple applying assembly 20 at a desired articulation angle. The articulation lock mechanism 200 reduces loads on the left and right actuating bladders 100, 102. In particular, a compression spring 202 is proximally positioned between a proximal end 204 of the articulation locking member 111 and the handle portion 22, biasing the articulation locking member 111 distally. Selective abutting engagement of a distal frictional surface distally projecting from the articulation locking member 111 engages a corresponding locking gear segment in a brake plate (not shown) received into a top proximal recess 220 of the articulating frame member 114.

The articulation lock mechanism 200 is described in greater detail in the commonly-owned U.S. patent application Ser. No. 11/194,437, "Surgical Instrument with an Articulation Shaft Locking Mechanism" to Wales et al., filed 1 Aug. 2005, the disclosure of which is hereby incorporated by reference in its entirety.

The elongate shaft 16 is depicted in an articulated position with the closure sleeve assembly 46 removed from around the frame assembly 44 and without the elongate channel 40 and anvil 42. Articulation actuator 80 is shown moved laterally to the left to compress right proximal reservoir bladder 90 and expanded distal right actuation bladder 100 moving T-bar 104 to the position shown. Thus, lateral movement of the articulation actuator 80 articulates the distal frame 114 clockwise about the single pivot frame ground 48 as shown. The articulation actuator 80 advantageously also automatically engages and disengages the articulation lock mechanism 200. In particular, a toothed detent surface 225 along a proximal top surface of the articulation actuator 80 receives an upwardly projecting locking pin 226 from the proximal end 204 of the articulation locking member 111. The engagement of the locking pin 226 within the root of the toothed detent surface 225 provides sufficient distal movement of the articulation locking member 111 for locking engagement. Lateral movement by an operator of the articulation actuator 80 proximally urges the locking pin 226 proximally, and thus disengages the articulation locking member 111 from the distal frame member 114. When the operator releases the articulation actuator 80, the locking pin 226 is urged by the compression spring 202 into the adjacent detent in detent surface 225 to lock the locking mechanism 111, and thereby the staple applying assembly 20, and to constrain the articulation mechanism 14 at a desired articulation position by constraining and expanding the inflated shape of the proximal left and right reservoir bladders 90, 92.

In use, a laterally moving articulation mechanism 230 is shown schematically in FIGS. 4-7 and includes a fluid control system 235 having fluid filled parallel left and right fluid bladders 236, 238 extending longitudinally therein that move a lateral member or T-bar 240 laterally by the movement of fluids 242. All directions are in reference to the longitudinal axis. Referring to the unarticulated view of FIGS. 4 and 5, the distally located end effector 232 pivots about pin 244 and has a gear segment 246 at a proximal end. Pivot pin 244 is attached to a frame (not shown). A rack 248 at a distal end of the T-bar 240 operably engages gear segment 246. T-bar 240 and rack 248 are laterally moveable along axis A-A. A distal portion of the long left and right fluid bladders 236, 238 lies laterally to the laterally moveable T-bar 240 and are laterally constrained within a closure sleeve 250 and vertically constrained by a frame 252 below and a spacer 254 above. Left actuating fluid bladder 236 is filled with fluid 242 and has left distal actuating bladder 256, left fluid passageway 258, and a left proximal reservoir bladder 260. Right fluid bladder 238 contains fluid 242 and has a right distal actuating bladder 262, right fluid passageway 264, and right proximal reservoir bladder 266. A fixed divider 270 extends from the frame 252 and separates the bladders 260, 266 and the fluid passageways 258, 264. The fixed divider 270 and the closure sleeve 250 constrain the fluid passageways 258, 264 and prevent expansion in the fluid passage sections 258, 264 of the bladders 236, 238. A laterally moveable "C"-shaped compression member 272 is included in articulation control mechanism 230 for the compression of one of the proximal reservoir bladders 260, 266 and the articulation of the end effector 232. In addition, other components such as a firing bar 274 passing through a firing bar slot 276 in the frame 252 may be incorporated (FIGS. 5, 7).

Figure 8:
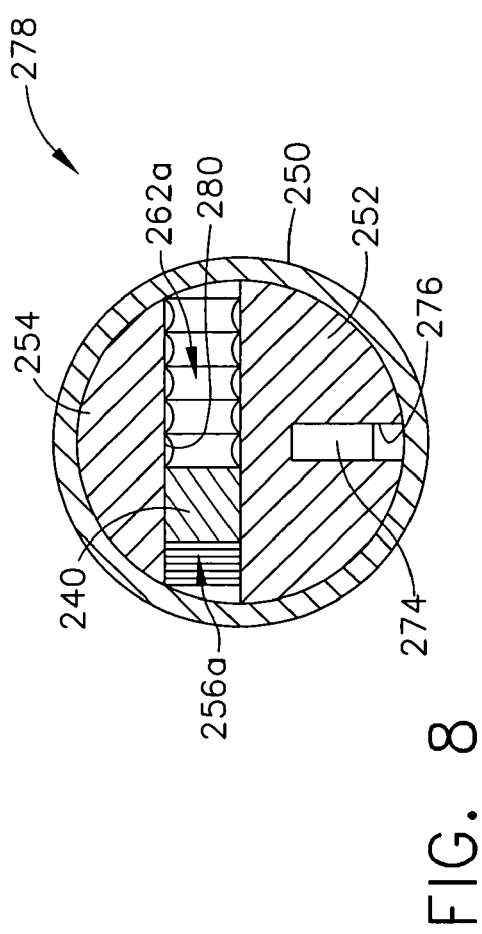
FIG. 8 is a back, cross-section view in elevation of a tubular shaft of the surgical instrument of FIG. 1 taken along lines 8-8 alternatively incorporating a pair of collapsible bellows for bladders and showing the T-bar in an articulated position with a right bellows expanded and a left bellows collapsed.

Rather than a rounded rectangular shape, the cross sectional shape of a bladder may be modified to be any shape. For example it could be advantageous to construct the distal and/or proximal bladders as a pleated bellows. In FIG. 8, a tubular shaft 278 for the surgical instrument 10 is as described above for FIGS. 4-7 with the exception that a left actuating bladder 256a and a right actuating bladder 262a are both of a rectangular pleated design with the former shown in a compressed state and the latter shown in an expanded state in a lateral cavity 280. Pleated right actuating bellows 262a collapse easily into the confined area of the right portion of the lateral cavity 280 as depicted. Similarly, pleated left actuating bellows 256a expand easily to fill the area of left portion of the lateral cavity 280. While not shown, pleated bladders may also be used for the proximal reservoir bladders. It should be appreciated that actuating bladders and distal bladders may be formed into other cross sectional shapes such as rounds, squares, triangles, hexagons, octagons, or any other shape that meets the needs of the mechanism.

Fluid Bladders. It should be appreciated with the benefit of the present disclosure that such bladders may be constructed in various ways from various combinations of materials. While shown as a unified part above, these bladders may be assembled from multiple parts or constructed as a single unitary fluid bladder. For multiple part construction, at least one of the bladders may be attached to any of the other elements. Many leak proof attachment methods are available for assembly such as welding, glue, press fit, heat staking, crimp fittings, clamps fittings, joints and the like. Two basic types of fluid bladders may be constructed. One is a high pressure, non-elastic rigid bladder from either rigid or elastomeric materials, and the other is a lower pressure elastomeric balloon.

Rigid balloon materials are known in the medical arts and are used for dilation or angioplasty or the expansion of stents within blood vessel walls. Rigid balloons are made from non-compliant or low compliant materials that retain their designed size and shape under high-pressure loading. Typically, these balloons are thin walled and are formed from high tensile materials with low elongation. Typical materials for these balloons are polyvinyl chloride (PVC), cross linked polyethylene, and polyester (PET) polyethylene terrapthalate, nylon and others. For angioplasty balloons, thin walled sections of PET tubing may be blow molded into a balloon shape. Each of the left and right fluid bladders may be formed from a continuous piece of thin walled tubing with both the proximal and distal bladders formed by expanding local sections of the thin walled tubing. Expansion of the proximal and distal bladder areas may be accomplished by locally heating the tubing and blow molding the bladder shapes therein. One of the open ends of the formed fluid bladders may then be sealed, and the other open end of the bladders may act as a fill port for fluids. After filling, the open fill port is sealed. Alternately, the fluid bladders may be assembled from multiple pieces rather than a single piece. Non-bladder portions of the fluid bladders, such as fluid passageways, may be formed from rigid or semi-rigid tubing or other materials.

Alternately, elastomeric balloons may also be used to construct fluid bladders. These elastomeric materials are formed into a first shape and, with the application of pressure, may expand to a larger shape. Elastomeric materials may expand and return to the original shape a number of times without degradation of the elastomeric properties. While not able to handle pressures as high as rigid materials, elastomeric bladders may be used to articulate. Confining or constraining the elastomeric fluid bladders between walls or constraints prevents bulging of bladder material into unwanted areas and increases the forces that may be applied. Elastomeric bladders may be constructed by various processes including dip molding or, like IV bags, formed from two sheets that are welded or glued together. Elastomeric bladders may be formed from latex, rubber, silicone, polyurethane, polyethelene, polypropelene, Teflon, or any one of a number of elastic or semi-elastic engineering materials.

Additionally, conventional blow molding techniques may be used to form bladders. Unlike the thin walled PET shrink tubing used in angioplasty balloons, conventional blow molding techniques use a hollow tube or molded hollow preform that is heated and moved to an injection station where low pressure air is typically used to initially inflate the rod or preform. A burst of high-pressure gas is then applied to force the expanded hot tube or preform into contact with the walls of the mold to cool the blown material in the net shape. While producing thin walls, the preform blow molding process produces thin walls that are much thicker than the less than 4 mil angioplasty balloons. This process forms many current products such as soda bottles, disposable pipettes with a rigid tube and expanded bladder, and containers. For the formation of bladders, a preform shape is first injection molded with the appropriate material thickness at the expandable bladder areas to provide the desired wall thickness when the bladders are expanded in the blow molding process. Once the bladders are blow molded into net shape, they may be filled with fluid and sealed. Appropriate blow molding materials include nylon, polyester (PET), polyethelene, polyprolelene, high density polyethelene (HDPE) and any one of a number of known blow molding materials.

In addition to rigid and elastomeric bladders, bladder construction may be springy or flaccid. That is, at least one of the proximal bladders or at least one of the distal bladders may be constructed from a spring material that wants to resume its original shape after compression and release. Alternately, at least one of the proximal bladders or at least one of the distal bladders may be constructed from a generally flaccid material. Such materials have a weak spring rate, if any, and do not tend to expand back to the original pre-deformed shape. Flaccid bladders or springy bladders may advantageously include the internal compression spring that forces the walls of the bladder outward. The internal compression spring may be formed from a variety of materials including metallic springs, plastic springs, foams, squeezable elastomerics and the like. A sealed assembly of a full flaccid bladder with a partially filled spring bladder (on a passageway) results in the spring bladder expanding and drawing fluid from the flaccid bladder. Assembly of a pair of partially compressed spring bladders (of equal spring rate walls and size) results in both spring bladders being in the partial compressed position. Compression of one of the partially filled spring bladders results in full expansion of the uncompressed spring bladder and reduction of the compressed spring bladder. Release of the compressed spring bladder enables the compressed spring bladder to expand and draw fluid back into the compressed spring bladder. This process is spring rate controlled and if both bladders have the same spring rate, the fluid will be drawn back into the released compressed spring bladder until both spring bladders are equally filled. If desired, mismatched spring rates for the spring bladders may be used to draw and store fluids into one of the bladders as desired.

Figure 9:
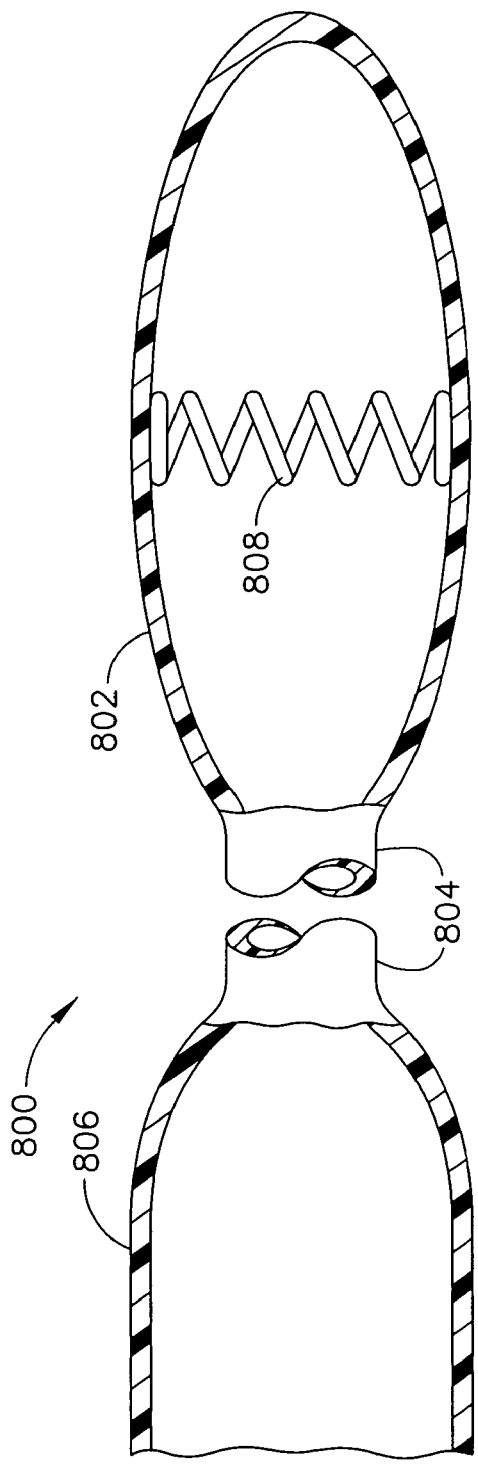
FIG. 9 is a longitudinal cross section view of a communicating combination of a reservoir bladder and an actuating bladder for the surgical instrument of FIG. 1 with one bladder expansively biased by containing a lateral compression spring.

In FIG. 9, as an example of an added resilient structure, a bladder 800 is depicted to include an actuating bladder 802 in fluid communication through a fluid passage or conduit 804 to a reservoir bladder 806. In this illustrative version, a compression spring 808 laterally biases the actuating bladder 802 to an expanded state. Advantageous features of the compression spring 808 includes providing a restoring force to expand bladder 802 or to center an end effector (not shown), as well as other advantages. If desired, springs may be placed in either one of both bladders 802, 806 or in both bladders 802, 806.

In FIG. 10, an alternate resilient structure, depicted as an open cell foam 810, fills the actuating bladder 802 rather than using a compression spring. Thus, fluid may be forced into and out of the open cell foam 810 as desired for expansion with the open cell foam 810 providing a degree of resilience.

In FIG. 11, a metal-walled bladder 900 may be formed from metal tubing 902 that is heated and pressure blown with a plugged end 904 either closed by a plug 906 before or after forming of an enlarged portion 908. The dimensions of the enlarged portion 908 may be controlled by selecting the temperature of heating, the amount of the metal tubing 902 that is heated, and/or surrounding the metal tubing 902 with a fixture (not shown) that constrains expansion to desired outer diameters for a neck portion 910, the enlarged portion 908, and the plugged end 904. Resulting thinner walls 912 of the enlarged portion 908 provides a desired degree of flexibility as a trade-off with burst strength deemed suitable for a fluid reservoir or actuator.

Figure 12:
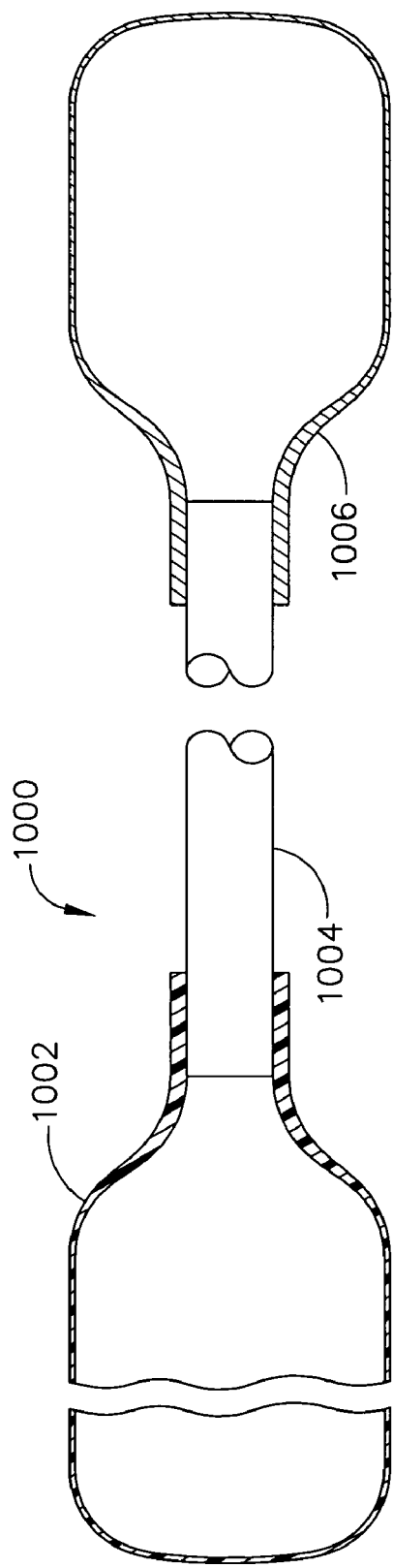
FIG. 12 is a longitudinal cross section view of a communicating combination of a reservoir bladder and actuated bladder assembled from different materials for the surgical instrument of FIG. 1.

In FIG. 12, a fluid control assembly 1000 may be assembled from a flaccid bladder 1002 that communicates via a rigid conduit 1004 to a deformable bladder 1006. The deformable bladder 1006 may be advantageously formed of a shape memory alloy (SMA) which are metals, such as NiTi (Nickel-Titanium), CuZnAl, and CuAlNi. SMAs exhibit two very unique properties: shape memory effect and pseudo-elasticity, made possible through a solid state phase change, that is a molecular rearrangement, which occurs in the shape memory alloy. In most SMAs, a temperature change of only about 10° C. is necessary to initiate a phase change between Martensite and Austenite.

Martensite, the relatively soft and easily deformed phase of SMAs, exists at lower temperatures. Austenite, the stronger phase of shape memory alloys, occurs at higher temperatures. The shape of the Austenite structure is cubic. The un-deformed Martensite phase is the same size and shape as the cubic Austenite phase on a macroscopic scale, so that no change in size or shape is visible in shape memory alloys until the Martensite is deformed. The temperatures at which each of these phases begin and finish forming are represented by the following variables: $M_s$, for the temperature at which Marsenite starts to form; $M_f$, for the temperature at which Marsenite finishes forming; and $A_f$, for the temperature at which Arsenite finishes forming. The shape memory effect is observed when the temperature of a piece of shape memory alloy is cooled to below the temperature $M_f$. At this stage, the alloy is completely composed of Martensite which can be easily deformed. After distorting the SMA, the original shape can be recovered simply by heating the wire above the temperature $A_f$. The heat transferred to the wire is the power driving the molecular rearrangement of the SMA, similar to heat melting ice into water, but the SMA remains solid. The deformed Martensite is now transformed to the cubic Austenite phase, which is configured in the original shape of the wire.

Pseudo-elasticity occurs in SMAs when the SMA is completely composed of Austenite (temperature is greater than $A_f$). Unlike the shape memory effect, pseudo-elasticity occurs without a change in temperature. The load on the SMA is increased until the Austenite becomes transformed into Martensite simply due to the loading. The loading is absorbed by the softer Martensite, but as soon as the loading is decreased, the Martensite begins to transform back to Austenite since the temperature of the wire is still above $A_f$, and the wire springs back to its original shape.

Thus, the deformable bladder 1006 may be deformed by fluid pressure and/or mechanical pressure with the shape memory effect or pseudo-elasticity relied upon to restore the deformable bladder 1006 to a desired shape (e.g., compressed or expanded). The flaccid bladder 1002 transfers a corresponding amount of fluid through the rigid conduit 1004 in proportion to the change in volume of the deformable bladder 1006. Either the flaccid bladder 1002 or the deformable bladder 1006 may serve as an actuating bladder with the other serving as a reservoir bladder having a controlled volume. For example, a deformable bladder 1006 (i.e., actuating bladder) may be formed to have a pleated, compressed state that is then heat treated to remember that shape. Alternatively, the deformable bladder 1006 may formed to have an expanded shape and then be deformed to a compressed state.

Figure 13:
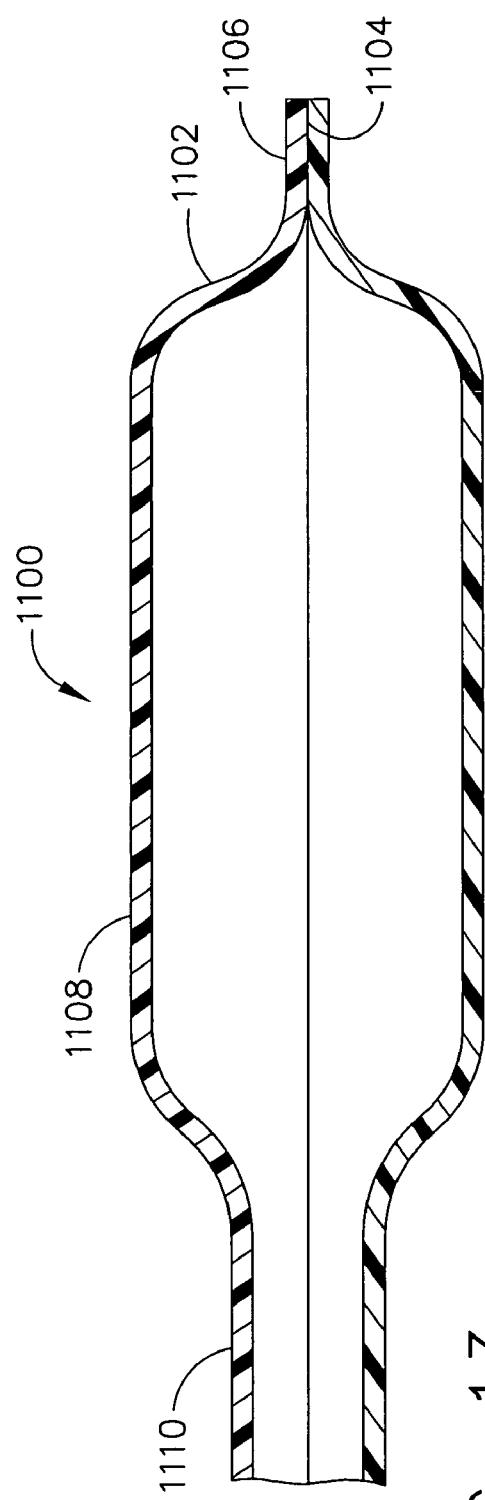
FIG. 13 is a longitudinal cross section view of a bladder formed from expanded tubing material having a communicating end and a heat or glue sealed end for the surgical instrument of FIG. 1.

In FIG. 13, an alternative flaccid or resilient bladder 1100 is formed from longitudinally continuous tubing material 1102 by heat sealing or internally gluing an inner diameter 1104 of one end 1106 that is held closed and flattened until cooled and/or set to form a non-communicating seal. An expanded portion 1108 of the tubing material 1102 communicates through a neck portion 1110.

Figure 14:
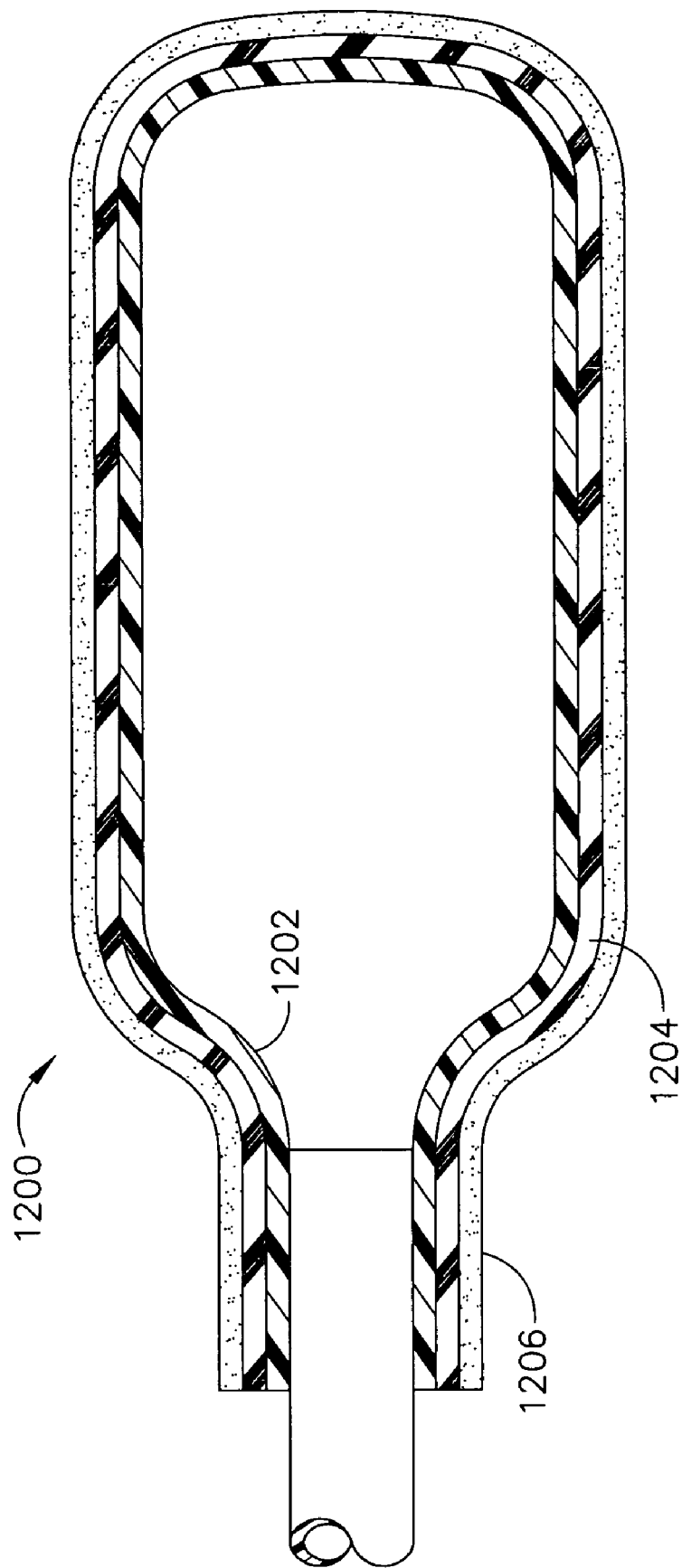
FIG. 14 is a longitudinal cross section view of a bladder formed from laminated materials including an inner blow molded plastic layer, intermediate resilient layer, and a lubrication layer for the surgical instrument of FIG. 1.

In FIG. 14, a further alternative laminate bladder 1200 that may be advantageously used in the surgical instrument of FIG. 1 is formed from a blow molded inner plastic layer 1202 with sufficient strength to define an expanded shape of the bladder 1200. A resilient layer 1204, such as Latex rubber, encompasses the inner plastic layer 1202 to provide additional strength and perhaps a compression force to bias the bladder 1200 toward a smaller volume. An outer lubricant layer 1206 (e.g., silicone, Teflon) assists in assembling the bladder 1200 into a surgical instrument (not shown) and is used to avoid binding/adhesion to walls of a bladder cavity that could cause improper expansion or contraction.

Alternately, whereas a three-layer laminated bladder is described above with the layers in a selected order, laminated bladders can be made from any two or more layers and the order of the layers and layer materials can be varied to suit the needs of the surgical instrument. For example, it can be advantageous to add an additional lubricated layer as the innermost layer to the three layers 1202, 1204, and 1206 listed above for a dry fluid such as microparticles (described below), or to use an inner protective layer on an outer metal layer to act as a barrier between the metal and fluid.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, a single reservoir bladder may serve as both a left and right actuating bladder as described in the aforementioned and incorporated U.S. patent application Ser. No. 11/061,908 entitled "SURGICAL INSTRUMENT INCORPORATING A FLUID TRANSFER CONTROLLED ARTICULATION MECHANISM" to Kenneth Wales and Chad Boudreaux filed on 18 Feb. 2005.

For another example, reservoir and/or actuating bladders may be incorporated into a surgical instrument for purposes other than articulation, such as for opening and/or closing an anvil of a stapling and severing end effector as described in commonly owned and co-pending U.S. patent application Ser. No. 11/165,094, entitled "SURGICAL INSTRUMENT HAVING FLUID ACTUATED OPPOSING JAWS" to Wales et al., filed 23 Jun. 2005, the disclosure of which is hereby incorporated by reference in its entirety.

As yet another example, a single fluid transfer approach may be incorporated wherein a single fluid actuator expands and compresses to effect articulation, perhaps assisted by a resilient opposing member that is not in fluid or pneumatic communication with the handle. An application consistent with such a design, for instance, could include just one bladder attached to a T-bar so that when compressed by the withdrawal of fluid, it pulls the T-bar with it.

As yet a further example, fluids used in a laterally moving device may be either compressible or incompressible. As used herein, the term "fluid" comprises liquids, gases, gels, microparticles, and any other material which may be made to flow between a pressure gradient. While any fluid may be used, sterilized solutions such as saline, mineral oil or silicone are illustrative flowable materials.

What is claimed is:

1. A surgical instrument, comprising:
a handle containing a reservoir;
a control attached to the handle, wherein the control is positionable to vary an internal volume of the reservoir;
a fluid conduit in fluid communication with the reservoir, wherein the fluid conduit is configured to communicate fluid in a longitudinal direction in response to the control varying the internal volume of the reservoir;

an elongate implement portion extending distally from the handle and defining a longitudinal axis, the elongate implement portion sized for insertion through a cannula to reach internal tissue and containing a bladder cavity distally spaced from the reservoir, wherein at least a portion of the elongate implement portion is substantially rigid and further comprises an articulating end effector;

a laterally actuated member attached to the elongate implement portion, the laterally actuated member being located within the bladder cavity and comprising an external motive surface, the laterally actuated member and the external motive surface being constrained to move in a direction lateral to the longitudinal axis, wherein the laterally actuated member further comprises a laterally movable end effector engagement feature configured to engage the end effector, wherein the end effector engagement feature is operable to articulate the end effector in response to lateral movement of the external motive surface; and an actuator in fluid communication with the reservoir via the fluid conduit, wherein the actuator is positioned distal to the reservoir, wherein the actuator is further positioned within the bladder cavity in the elongate implement portion, wherein the actuator is positioned laterally adjacent to the external motive surface of the laterally actuated member, wherein the actuator is operable to laterally actuate the laterally actuated member by exerting a lateral force on the external motive surface in response to longitudinal fluid transfer with transfer of fluid from the reservoir via the conduit, to thereby articulate the end effector;

wherein a selected one of a group consisting of the reservoir and the actuator comprises a bladder.

2. The surgical instrument of claim 1, further comprising a resilient structure contained by the bladder.

3. The surgical instrument of claim 2, wherein the resilient structure comprises a spring.

4. The surgical instrument of claim 2, wherein the resilient structure comprises a resilient foam.

5. The surgical instrument of claim 1, wherein the bladder comprises tubing material heated and blow molded to an enlarged diameter with one end sealed.

6. The surgical instrument of claim 5, wherein the one end is heat sealed.

7. The surgical instrument of claim 5, wherein the one end is adhesively sealed.

8. The surgical instrument of claim 5, wherein the tubing material comprises a metal tube.

9. The surgical instrument of claim 1, wherein the bladder comprises an injection molded hollow pre-form that is blow molded into a thin walled enlarged size.

10. The surgical instrument of claim 1, wherein the bladder comprises a shape memory alloy.

11. The surgical instrument of claim 10, wherein the bladder has an Austenite expanded shape deformed by fluid transfer with the reservoir to a contracted shape.

12. The surgical instrument of claim 10, wherein the bladder has an Austenite collapsed shape deformed by fluid transfer with the reservoir to an expanded shape.

13. The surgical instrument of claim 1, wherein the bladder comprises a laminate bladder.

14. The surgical instrument of claim 13, wherein the laminate bladder comprises a lubricant layer.

15. The surgical instrument of claim 13, wherein the laminate bladder comprises a blow molded plastic layer and a resilient layer.

16. The surgical instrument of claim 13, wherein the laminate bladder comprises at least two layers selected from a group consisting of a blow molded plastic layer, a resilient layer, and a lubricant layer.

17. A surgical instrument, comprising:

a handle containing a reservoir bladder;

a compression surface movably attached to the handle to vary an internal volume of the reservoir bladder;

an elongate implement portion extending distally from the handle and defining a longitudinal axis, the elongate implement portion sized for insertion through a cannula to reach internal tissue and containing a bladder cavity spaced distally from the reservoir bladder, the bladder cavity further comprising an inner cavity surface, wherein the elongate implement portion comprises an articulating end effector;

a fluid conduit in fluid communication with the reservoir bladder, wherein the fluid conduit extends longitudinally through at least a portion of the elongate implement portion;

an actuated member attached to the elongate implement portion and comprising an external motive surface constrained to move laterally without substantially moving longitudinally within the bladder cavity, wherein the actuated member further comprises an end effector engagement surface, wherein the end effector engagement surface is configured to engage the end effector, wherein the end effector engagement surface is further operable to move lateral to the longitudinal axis to articulate the end effector in response to lateral movement of the external motive surface; and an actuating bladder in fluid communication with the reservoir bladder via the fluid conduit, wherein the actuating bladder is positioned within the bladder cavity in the elongate implement portion, wherein the actuating bladder is further positioned distal to the reservoir, wherein the actuating bladder is operable to actuate laterally against the external motive surface of the actuating member and against the inner cavity surface thereby moving the external motive surface and the actuated member along the axis extending in a direction lateral to the longitudinal axis in response to longitudinal fluid transfer from the reservoir bladder via the fluid conduit.

18. The surgical instrument of claim 17, wherein the actuator bladder comprises a laminate bladder.

19. The surgical instrument of claim 17, wherein a selected one of the group consisting of the reservoir bladder and the actuating bladder further comprises an internal resilient structure.

20. The surgical instrument of claim 19, wherein the internal resilient structure comprises a spring.

21. The surgical instrument of claim 19, wherein the resilient structure comprises a resilient foam.

22. The surgical instrument of claim 17, wherein the selected one of the group consisting of the reservoir bladder and the actuator bladder comprises tubing material heated and blow molded to an enlarged diameter with one end sealed.

23. The surgical instrument of claim 22, wherein the tubing material comprises a metal tube.

24. The surgical instrument of claim 17, wherein the selected one of the group consisting of the reservoir bladder and the actuator bladder comprises an injection molded hollow pre-form that is blow molded into a thin walled enlarged size.

25. The surgical instrument of claim 17, wherein the actuator bladder comprises a shape memory alloy.

26. The surgical instrument of claim 25, wherein the actuator bladder comprises a laminate bladder.

27. The surgical instrument of claim 25, wherein the laminate bladder comprises an internal blow molded plastic layer, an intermediate resilient layer, and an outer lubricant layer.

28. The surgical instrument of claim 25, wherein the laminate bladder comprises a lubricant layer.

29. The surgical instrument of claim 25, wherein the laminate bladder comprises a blow molded plastic layer and a resilient layer.

30. The surgical instrument of claim 15, wherein the laminate bladder comprises at least two layers selected from a group consisting of a blow molded plastic layer, a resilient layer, and a lubricant layer.

31. A surgical instrument, comprising:
a handle containing a fluid source having first and second conduits extending distally therefrom;
a differential control movably attached to the handle to differentially vary fluid transfer from the fluid source to the first and second conduits;
an elongate implement portion extending distally from the handle and defining a longitudinal axis, the elongate implement portion sized for insertion through a cannula to reach internal tissue and containing first and second bladder cavities spaced distally from the fluid source, wherein the first and second bladder cavities are laterally adjacent to each other;
an actuated member attached to the elongate implement portion and comprising a motive surface positioned longitudinally between the interconnected first and second bladder cavities, the actuated member being constrained to move within the bladder cavities in a direction lateral to the longitudinal axis, wherein lateral movement of the motive surface relative to the longitudinal axis increases the volume of one of the first and second bladder cavities and decreases the volume of the other one of the first and second bladder cavities;
a first actuating bladder in fluid communication with the first conduit and positioned distally therefrom within the first bladder cavity in the elongate implement portion, wherein the first actuating bladder is configured to actuate against the motive surface of the actuating member in a first direction along an axis lateral to the longitudinal axis in response to longitudinal fluid transfer from the first conduit; and
a second actuating bladder in fluid communication with the second conduit and positioned distally therefrom within the second bladder cavity in the elongate implement portion, wherein the second actuating bladder is configured to actuate against the motive surface of the actuating member in a second direction along an axis lateral to the longitudinal axis in opposition to the first direction in response to longitudinal fluid transfer from the second conduit.

\* \* \* \* \*